US005636317A

United States Patent [19]

Reznik

[11] Patent Number: 5,636,317
[45] Date of Patent: Jun. 3, 1997

[54] ELECTROHEATING APPARATUS AND METHODS

[76] Inventor: David Reznik, 12690 Viscaino Rd., Los Altos Hills, Calif. 94022

[21] Appl. No.: 453,988

[22] Filed: May 30, 1995

Related U.S. Application Data

[62] Division of Ser. No. 252,120, Jun. 1, 1994.

[51] Int. Cl.$^6$ .............................. H05B 3/03; A23L 1/025
[52] U.S. Cl. .................... 392/312; 392/315; 392/338; 426/244; 99/358
[58] Field of Search .......................... 219/780, 772; 392/315, 316, 317, 318, 319, 320, 321, 311, 312, 313, 314, 338; 426/244; 99/358, 351, DIG. 14

[56] References Cited

U.S. PATENT DOCUMENTS

| | | |
|---|---|---|
| 535,267 | 3/1895 | Wagner et al. . |
| 684,746 | 10/1901 | Chapman . |
| 731,339 | 6/1903 | Rudd . |
| 1,147,558 | 7/1915 | Shelmerdine . |
| 1,360,447 | 11/1920 | Chapman . |
| 1,431,580 | 10/1922 | Graetzer et al. . |
| 1,522,188 | 1/1925 | Hull . |
| 1,775,579 | 9/1930 | Woodrich . |
| 1,813,064 | 7/1931 | Matzka . |
| 1,934,703 | 11/1933 | Golden . |
| 2,081,243 | 5/1937 | Macy . |
| 2,438,582 | 3/1948 | Southerwick . |
| 2,472,708 | 6/1949 | Jones . |
| 2,473,041 | 6/1949 | Urbain et al. . |
| 2,495,415 | 1/1950 | Marshall . |
| 2,510,796 | 6/1950 | Brown . |
| 2,550,584 | 4/1951 | Mittelmann . |
| 2,564,579 | 8/1951 | Parmenter et al. . |
| 2,565,311 | 8/1951 | Koonz et al. . |
| 2,582,281 | 1/1952 | Robertson . |
| 2,585,970 | 2/1952 | Shaw . |
| 2,685,833 | 8/1954 | Hagopian . |
| 2,799,216 | 7/1957 | Coulter ..................................... 99/253 |
| 2,838,640 | 6/1958 | Mann et al. . |
| 3,315,681 | 4/1967 | Poppendiek . |
| 3,327,086 | 6/1967 | Cable . |
| 3,625,843 | 12/1971 | Doevenspeck . |
| 3,632,962 | 1/1972 | Cherniak . |
| 3,664,929 | 5/1972 | White et al. . |
| 3,709,802 | 1/1973 | Okuhara et al. . |
| 3,753,886 | 8/1973 | Myers . |

(List continued on next page.)

FOREIGN PATENT DOCUMENTS

| | | |
|---|---|---|
| 2100618 | 1/1994 | Canada . |
| 0032840 | 7/1981 | European Pat. Off. . |

(List continued on next page.)

OTHER PUBLICATIONS

Palaniappan, S., "Ohmic Heating of Foods: Studies on Microbicidal Effect of Electricity, Electrical Conductivity of Foods, and Heat Transfer In," Ph.D. Thesis, The Ohio State University, 1991.

Palaniappan, S. et al., "Effects of Electricity on Microorganisms: A review," Journal of Food Processing and Preservation vol. 15, No. 5 (Oct., 1990), pp. 383–414.

(List continued on next page.)

*Primary Examiner*—Philip H. Leung
*Attorney, Agent, or Firm*—Fish & Neave; Jeffrey H. Ingerman

[57] ABSTRACT

Electroheating apparatus and methods utilize a dielectric structure defining a conduit course of relatively small cross-sectional area and electrode surfaces of relatively large area so that the electrical current density in a region of the conduit remote from the electrodes is substantially higher than the current density at the electrode surfaces themselves. The system uses relatively high electrical resistance and relatively high voltages to provide substantial heating effect with low total currents. Foods such as liquid egg can be pasteurized.

23 Claims, 5 Drawing Sheets

U.S. PATENT DOCUMENTS

| | | | |
|---|---|---|---|
| 3,796,857 | 3/1974 | Henley et al. | 392/312 |
| 3,855,531 | 12/1974 | Fielibert et al. | |
| 3,859,981 | 1/1975 | Yoshida | 126/374 |
| 3,867,610 | 2/1975 | Quaintance | |
| 3,877,360 | 4/1975 | Vigerstrom | |
| 3,919,052 | 11/1975 | Fresnel et al. | 195/115 |
| 3,949,099 | 4/1976 | Kaufman | |
| 4,091,119 | 5/1978 | Bach | |
| 4,109,566 | 8/1978 | Vigerstrom | |
| 4,177,719 | 12/1979 | Balaguer | |
| 4,211,887 | 7/1980 | Williamson | 13/6 |
| 4,251,715 | 2/1981 | Petersson et al. | |
| 4,260,874 | 4/1981 | Will | |
| 4,369,351 | 1/1983 | Massey et al. | 219/284 |
| 4,378,846 | 4/1983 | Brock | |
| 4,386,110 | 5/1983 | Komeyasu et al. | |
| 4,417,132 | 11/1983 | Simpson | 219/291 |
| 4,420,382 | 12/1983 | Riedl | |
| 4,434,357 | 2/1984 | Simpson et al. | 219/291 |
| 4,457,221 | 7/1984 | Geren | |
| 4,496,594 | 1/1985 | Miyahara | |
| 4,522,834 | 6/1985 | Miyahara | |
| 4,524,079 | 6/1985 | Hofmann | |
| 4,695,472 | 9/1987 | Dunn et al. | 426/237 |
| 4,723,483 | 2/1988 | Papchenko et al. | |
| 4,739,140 | 4/1988 | Reznik | 219/10.81 |
| 4,808,425 | 2/1989 | Swartzel et al. | 426/399 |
| 4,838,154 | 6/1989 | Dunn et al. | 99/451 |
| 4,853,238 | 8/1989 | Huang | |
| 4,857,343 | 8/1989 | Hekal | |
| 4,871,559 | 10/1989 | Dunn et al. | |
| 4,927,994 | 5/1990 | Leger | |
| 4,953,536 | 9/1990 | Israelsohn et al. | |
| 4,957,759 | 9/1990 | Swartzel et al. | |
| 4,957,760 | 9/1990 | Swartzel et al. | |
| 4,959,525 | 9/1990 | Stirling et al. | |
| 4,971,819 | 11/1990 | Miyahara | |
| 4,971,827 | 11/1990 | Huang | |
| 4,994,291 | 2/1991 | Swartzel et al. | |
| 5,019,407 | 5/1991 | Swartzel et al. | |
| 5,019,408 | 5/1991 | Swartzel et al. | |
| 5,048,404 | 9/1991 | Bushnell et al. | 99/451 |
| 5,084,153 | 1/1992 | Mosse et al. | |
| 5,085,882 | 2/1992 | Rausing | |
| 5,091,152 | 2/1992 | Thomas, Sr. | |
| 5,105,724 | 4/1992 | Swartzel et al. | |
| 5,167,976 | 12/1992 | Papetti | |
| 5,226,106 | 7/1993 | Stirling | 392/314 |
| 5,235,905 | 8/1993 | Bushnell et al. | 99/451 |
| 5,266,338 | 11/1993 | Cascione et al. | |
| 5,288,471 | 2/1994 | Corner | |
| 5,290,583 | 3/1994 | Reznik et al. | |
| 5,326,530 | 7/1994 | Bridges | |
| 5,415,882 | 5/1995 | Knipper et al. | 426/237 |
| 5,514,391 | 5/1996 | Bushnell et al. | 426/237 |

FOREIGN PATENT DOCUMENTS

| | | |
|---|---|---|
| 0457179 | 11/1981 | European Pat. Off. |
| 230978A | 1/1986 | European Pat. Off. |
| 0497099 | 8/1992 | European Pat. Off. |
| 0685987 | 12/1995 | European Pat. Off. |
| 2513087 | 3/1983 | France |
| 945582 | 7/1956 | Germany |
| 1075570 | 11/1957 | Germany |
| 47-48542 | 6/1972 | Japan |
| 24735 | 2/1931 | Netherlands |
| 639158 | 12/1978 | U.S.S.R. |
| 683034 | 3/1979 | U.S.S.R. |
| 895141 | 5/1962 | United Kingdom |
| 904371 | 8/1962 | United Kingdom |
| 2068200 | 8/1981 | United Kingdom |
| 2147776 | 5/1985 | United Kingdom |
| 2164732 | 3/1986 | United Kingdom |
| 2282052 | 3/1995 | United Kingdom |
| WO89/00384 | 1/1989 | WIPO |
| WO9015547 | 12/1990 | WIPO |
| WO93/19620 | 10/1993 | WIPO |
| WO94/11681 | 5/1994 | WIPO |
| WO94/18845 | 9/1994 | WIPO |
| WO95/10943 | 4/1995 | WIPO |

OTHER PUBLICATIONS

Palaniappan, S. et al., "Experimental Studies on Electroconductive (Ohmic) Heating of Liquids," prepared for an American Society of Agricultural Engineers Meeting Presentation (Dec. 12–15, 1989), Paper No. 89–6553.

Parrott, D.L. et al., "The Aseptic Processing of Fluids Containing Particulates from 1/8" to 1 size, prepared for presentation at American Institution of Chemical Engineers 1988 Summer Meeting (Aug. 21–24, 1988) (Unpublished), Paper No. 60e.

Reznik, D., "Electroheating," Dec., 1989.

Sastry, S.K., "A Model for Heating of Liquid–Particle Mixtures in a Continous Flow Ohmic Heater," Journal of Food Process Engineering 15 (1992), pp. 263–278.

Sastry, S.K. et al., "Mathematical Modeling and Experimental Studies on Ohmic Heating of Liquid–Particle Mixtures in a Static Heater," Journal of Food Process Engineering 15 (1992), pp. 241–261.

Alkskog, L., "High Temperature pasteurization of Liquid Whole Egg," Process Technology, pp. 16–18.

Hamid–Samimi, M.H. et al., "Aseptic Packaging of Ultra-pasteurized Egg, Design and Economic Considerations," publication date unknown, but a copy was transmitted to Mr. Merle Kirk under cover of a letter dated Aug. 21, 1985 from Prof. Hersell Ball, Jr.

Hanson et al., "Pasteurization Of Liquid Egg Products," Received for publication Nov. 16, 1946 pp. 277–283.

Madsen, M., "Pasteurizing of Egg Products," Sundhedsplejen (Dec., 1958), 102–105 and translation thereof.

Murdock et al., "The Pasteurization Of Liquid Whole Egg," issued from the Office of Medical Research Council, 38, Old Queen Street, Westminster, S.W.I.

Russell, M.J., "Live Long and Prosper," Food Engineering, Dec., 1992, pp. 77–80.

Winter et al., "Pasteurization of Liquid–Egg Products. I. Bacteria Reduction in Liquid Whole Egg and Improvement in Keeping Quality," Journal Paper No. J–1300 of the Town Agricultural Experimental Station, received from publication on Jun. 18, 1945, 229–245.

Winter et al., "Pasteurization of Liquid Egg Products III. Destruction of Salmonella in Liquid Whole Egg," American Journal of Public Health, vol. 36, pp. 451–460 (1946).

"Annual Report of Cooperative Regional Projects" Supported by Allotment of the Regional Fund, Hatch Act, as Amended Aug. 11, 1955, Jan. 1 to Dec. 31, 1984, Raleigh, North Carolina. Approved by Chairman Hershell Ball, Jr. on Mar. 14, 1985.

Ball, H.R. Jr. et al., "Function and Shelf Life of Ultrapasteurized, Aseptically packaged Whole Egg" Abstract, Poultry Science Association Annual Meeting–Jul. 29–Aug. 2, 1985, Iowa State Universtiy, Ames.

Dinnage, D.F., "Continuous Aseptic Processing Using the Ohmic Heating Process," Changing Food Technology 3, Food Technology: A view of the Future (Selected Papers from the Sixth Eastern Food Science & Technology Conference, Edited by Allen Freed (1990), pp. 29–41.

Essary, E.O. et al., "New Uses of Heated Aseptically Packaged Fluid Egg Products," Departments of Food Science and Technology, and Chemical Engineering, Virginia Polytechnic Institute of State University, Blacksburg, VA, 1983.

Hamid–Samimi, M.H., "Criteria Development for Extended Shelf–Life Pasteurized Liquid Whole Egg," Ph.D. Thesis, North Carolina State University, Raleigh, North Carolina, 1984.

Jacobs, L.C., "Aseptic packaging promises new role for pasteurized liquid eggs," Apr., 1981.

Still, M., "NCSU researchers crack the secret of long shelflife for eggs," *The News and Observer*, Raleigh, North Carolina, Sep. 3, 1985.

Stone, W.K. et al., "Aseptic Processing of Liquid Eggs Pasteurized in a Teflon Heat Exchanger," 1983.

Sastry, S.K. et al., "Ohmic Heating of Liquid–Particle Mixtrues," Food Technology, pp. 64–67, Dec. 1992.

Parrott, D.L., "Use of Ohmic Heating for Aseptic Processing of Food Particulates," Food Technology, pp. 68–72, Dec., 1992.

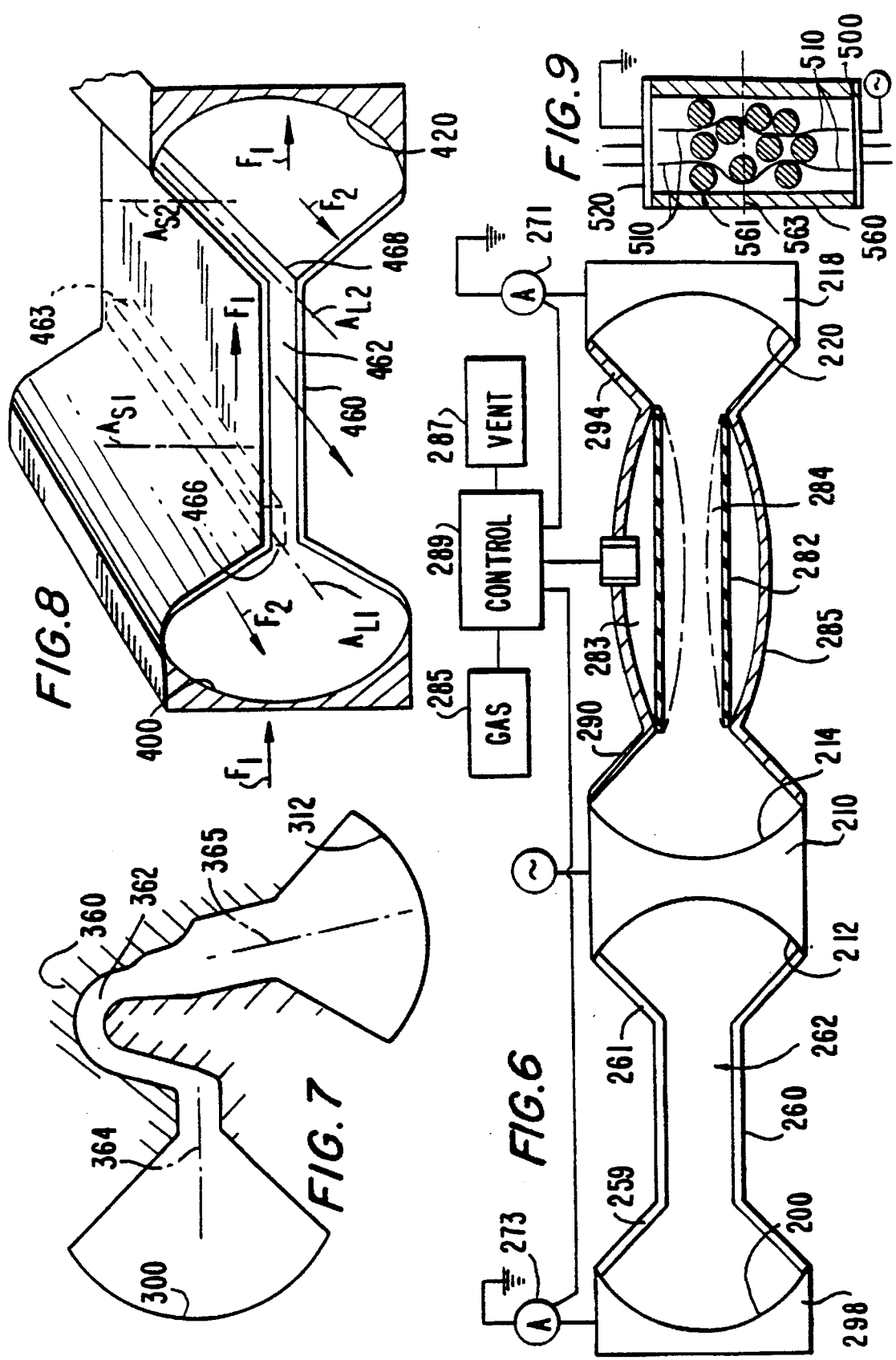

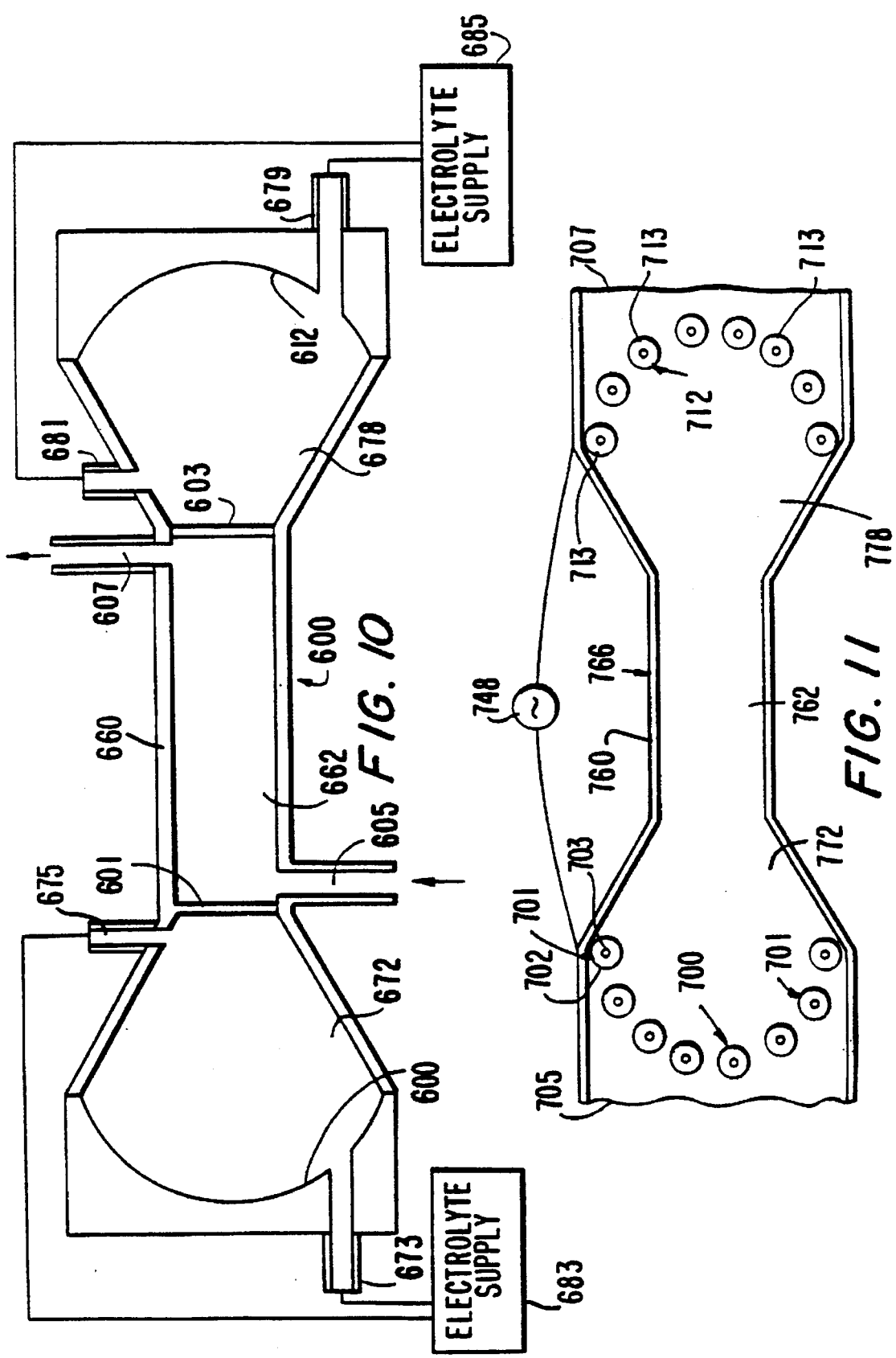

ELECTROHEATING APPARATUS AND METHODS

This is a division, of application Ser. No. 08/252,120, filed Jun. 1, 1994, entitled ELECTROHEATING APPARATUS AND METHODS.

FIELD OF THE INVENTION

The present invention relates to the field of electroheating of flowable materials, such as liquid foods and biological products by passage of electrical currents therethrough; to processes and apparatus for such electroheating and to bacteriological control procedures using such electroheating.

BACKGROUND OF THE INVENTION

Electroheating, also called "ohmic heating", "resistive heating" and "heating by electroconductivity" is a process wherein an electrically conductive material is heated by passing an electrical current through the material, so that electrical energy is converted to heat by the resistance of the material. Stated another way, the material itself acts as a resistance heater. Typically, the electrical current is passed through the material by applying an electrical potential to spaced apart electrodes in contact with the material.

Because heat is evolved within the material itself, the rate of heating is not limited by the rate of heat transfer through the boundary of the material, or by the rate of conduction within the material itself. Thus, electroheating theoretically can provide rapid and uniform heating.

One important application for electroheating is in pasteurization and similar bacteriological controlled processes applied to fluid foods and biological materials such as milk, whole egg, egg and milk products, soups, stews and the like. Industry practice and governmental regulations for processing such products typically require that the product be brought to a required minimum temperature and held at or above the required minimum temperature for a specified minimum holding period. However, many such products are thermally sensitive and if held near or above the required minimum treatment temperature for prolonged periods, the flavor, texture or usefulness of the product may be adversely affected. Accordingly, the product typically is preheated to a temperature below the required minimum temperature either by a conventional heat exchanger such as a plate heat exchanger, scraped surface heat exchange or the like. After preheating, the product passes through an electroheating apparatus where it is rapidly heated to above the required minimum temperature. After passage through the electroheater, the product passes through a holding zone, typically a long, thermally insulated pipeline. If the product is of a proper temperature at the exit of the holding zone, it is cooled rapidly and then packaged.

There are, however, substantial practical difficulties with electroheating of thermally sensitive materials. Passage of an electric current through many materials tends to cause electrolysis as, for example, conversion of water and salts in a food product to the constituent gases. This, in turn, tends to promote undesired side reactions in the food product leading to off-flavors. Further, with some electrode materials, electrolytic effects can lead to gradual dissolution of the electrode and contamination of the product with material from the electrode. As disclosed in U.S. Pat. No. 4,729,140, electrolytic effects in electroheating can be suppressed effectively by applying the electrical current at a frequency above the 50 cycle or 60 cycle AC commonly available from the power mains as, for example, a frequency between about 100 Hz and about 450 KHz. Typically, frequencies on the order of 100 KHz or more, in the radio frequency or "RF" range, are used. Although the use of RF power in electroheating does effectively suppress electrolysis, it requires costly frequency conversion apparatus.

Moreover, to avoid problems of product damage such as coagulation in the case of eggs and formation of local arcs within the apparatus, the energy input to electroheating apparatus has been limited. Merely by way of example, PCT Publication WO93/19620 suggests specifically that electroheaters should be operated so that the product temperature is raised within each electroheater by no more than about 15° C. and most preferably by more than about 5° C. and further teaches, as an example, a heater which can raise the product temperature only at the rate of "1° C. per second", a rate no higher than that achievable with conventional plate heat exchangers. Thus, heretofore, one approach which has been taken to achieving satisfactory results in electroheating has been to operate at relatively low current densities and, typically, at relatively low rates of energy input. Further electroheating apparatus and methods are described in U.S. Pat. No. 5,290,583.

Other electroheating apparatus which may be useful incorporate a series of concentric electroheating cells each incorporating a generally cylindrical outer electrode and rod-like inner electrode concentric with the outer electrode. In each such cell, the electrical potential is applied between the central, rod-like electrode and the outer electrode, so that the potential difference is generally radial. The apparatus may further include elongated "sight glass" cells, each including a dielectric pipe and electrodes contacting the fluid at opposite ends of the pipe. In one particularly useful arrangement the fluid to be heated first enters through one sight glass cell, then passes through the concentric cells in sequence and leaves the apparatus through the other sight glass cell. These sight glass cells operate at a relatively high potential, such as about 7800 volts whereas the concentric cells operate at about 200 volts potential. The concentric cells are connected electrically in parallel with one another. Apparatus of this nature using radio frequency ("RF") has been used successfully in treating whole egg and egg products. Millions of pounds of product have been successfully pasteurized using this electroheating apparatus and the resulting product has been widely accepted as having excellent flavor characteristics and storage stability.

Accordingly, despite the significant efforts and progress in the electroheating art there have still been significant needs for further improvements.

SUMMARY OF THE INVENTION

The present invention addresses these needs.

One aspect of the present invention provides methods of heating a conductive fluid. Methods according to this aspect of the invention may include the step of passing the fluid through a continuous course defined by the dielectric structure, the course having first and second ends, and simultaneously passing an electrical current between a first electrode surface adjacent the first end of the course and a second electrode surface adjacent the second end of the course. Preferably, the fluid passes along the course from the first end to the second end, so that the fluid moves co-directionally with the electrical current. These steps are conducted so that the electrical current density at a region of the course remote from the electrodes is substantially greater than the electrical current density at the electrode surfaces. The dielectric structure forming the continuous course serves to concentrate the current. Thus, the area of each electrode surface may be substantially greater than the cross-sectional area of the course in the region remote from the electrodes. Most preferably, the electrical current density is maintained substantially uniform over each electrode surface. The ratio of electrical current density in the aforementioned high-current density region of the course to the maximum current density at the electrode surfaces is desirably at least about 5:1, more preferably at least 10:1 and most preferably at least about 35:1 or more.

This aspect of the present invention incorporates the realization that many of the difficulties encountered heretofore in electroheating have been caused by phenomena occurring at and adjacent the electrode surfaces when the electrodes are subjected to relatively high current densities. Although the present invention is not limited by any theory of operation, it is believed that phenomena such as localized burning and sticking of the products being treated, arcing, and the like, are related at least in part to local instabilities such as boiling or "run away", in which localized overheating adjacent the electrode reduces the resistance of the material in one region, leading to concentration of the current in that region and further heating. Regardless of the reasons for the problems occurring at the electrode surfaces heretofore, these difficulties have generally been associated with high current densities. Thus, it has been necessary heretofore to operate the entire system at relatively low current density, both at the electrodes and within the product. In the preferred methods according to this aspect of the present invention however, the current density within the fluid material in the region of the course remote from the electrodes may be substantially higher than the current density at the electrodes. The current density within the fluid material may be substantially higher than that achievable in prior systems even where the total current is low.

Most preferably, the material being treated provides an electrical resistance between the electrode surfaces through the course of at least about 100 ohms, most preferably about 500 ohms and more preferably at least about 1000 ohms or more, and the electrical potential between the electrodes is at least about 220 volts, more preferably at least about 1000 volts and most preferably at least about 6000 volts or more.

Because the material in the course defines a relatively high resistance electrical current path between the electrodes, substantial power dissipation and hence substantial heating, can be achieved at relatively low current per unit material processed. At such low current levels, electrolysis is substantially eliminated and the system operates satisfactorily even where the current has very low or zero frequency. The electrical current used in the method desirably has frequency of less than about 400 Hz and more preferably less than about 100 Hz. Currents in the range below 100 Hz are commonly referred to as "mains frequency", as commercially available AC power commonly is supplied at these frequencies, most commonly at 50 Hz or 60 Hz. Because the method can be practiced using mains frequency power, the preferred methods can be practiced without the use of frequency conversion devices such as RF generators, microwave generators and the like.

Preferred methods according to the present invention can achieve substantial heating rates without destroying the product. Thus, a process according to a further aspect of the invention provides methods of heating a proteinaceous biological product by continuously supplying electrical energy to the product and conductively dissipating the electrical energy in the product at a rate of at least about 40 kilocalories per kilogram product per second. Still higher rates of energy dissipation and hence higher heating rates are more preferred. Methods according to this aspect of the present invention can be applied to a wide range of proteinaceous products but are particularly valuable in the case of liquid egg.

The term "liquid egg" in accordance with the present invention includes "liquid egg" includes liquid egg white, liquid egg yolk, or combinations thereof (referred to as "liquid whole egg") with or without additives such as salt, sugar, milk, stabilizers, antibiotics, dextrins, cyclodextrins, peroxides, acids such as citric acid and food including solid or particulate foodstuffs. Liquid egg from which cholesterol has been removed is also included referred to herein as "egg". Thus, the ability to apply electrical energy to egg at very high rates without damaging the product in the process allows very rapid heating of the egg as, for example, at a rate of at least about 100° C. per second and most preferably at least 200° C. per second or more.

Preferred processes according to this aspect of the invention provide electroheating at rates many times those employed heretofore. The higher heating rates allow high-temperature, short-time pasteurization of the material being treated. This helps to preserve product quality. This aspect of the invention further includes microbial control processes for egg and other proteinaceous materials. Moreover, although the present invention is not limited by any theory of operation, electrical current itself is believed to have a beneficial effect in damaging and/or killing microorganisms, particularly bacteria. That is, products pasteurized or otherwise treated using electroheating procedures in which a current is passed through the material tend to have longer shelf lives, under otherwise comparable conditions, than products treated at the same temperatures but with only non-electrical heating. In preferred processes according to this aspect of the present invention this effect is accentuated by the concentration of current within the material remote from the electrodes. Thus, even where the current density at the electrodes is relatively low the current density within the product remote from the electrodes will be substantial. Moreover, in the preferred embodiments where the material flows through an elongated conduit or other course, the material can be exposed to the passage of the electrical currents for an appreciable time.

A further aspect of the present invention provides electroheating apparatus. Electroheating apparatus according to this aspect of the invention may include a dielectric structure defining an elongated first conduit having inlet and outlet ends and may also include means defining first and second electrode surfaces disposed adjacent to ends of the first conduit so that a conductive fluid material passing through the first conduit will contact the first and second electrode surfaces. At least one of the electrode surfaces desirably is disposed outside of the adjacent end of the first conduit and at a substantially uniform distance from the end of first conduit. This electrode surface preferably has area greater than the minimum cross-sectional area of the first conduit, and desirably greater than the mean cross-sectional area of the first conduit. Most preferably, both of the electrode surfaces are disposed outside of the adjacent end of the first conduit and at a substantially uniform distance from the conduit and each of the electrode surfaces has area greater than the mean cross-sectional area of the conduit.

In this apparatus, the fluid material in the conduit will have a greater electrical resistance than the fluid adjacent the electrode surfaces. Electrical energy applied through the electrodes will be converted to heat principally in the conduit. Preferably, the conduit has a central axis at each end and each electrode surface is generally in the form of a surface of revolution about the central axis of the adjacent end of the conduit. Most desirably, each electrode surface is generally in the form of a surface region of a sphere having its center on the central axis of the adjacent conduit end.

The dielectric structure desirably includes a transition section associated with each end of the conduit, the transition section extending from the end of the conduit towards the electrode surface of the electrode associated with such conduit end. This wall structure desirably defines a transition passageway of progressively increasing cross-sectional area in the direction from the end of the conduit towards the associated electrode. Thus, the wall structure may be generally in the form of a surface of revolution such as a cone, paraboloid or the like having progressively increasing diameter in the direction from the end of the conduit towards the electrode surface. The electrode means preferably includes an electrode bodies defining the first and second electrode surfaces. The wall structure of the transition section desirably extends to the associated electrode surface and is connected to the electrode around the periphery of the electrode surface. The electrode may have one or more ports extending through the electrode surface so that a conductive fluid to be heated can be passed through the port of one electrode, through one transition passageway through the first conduit and through the other transition passageway and the port of the other electrode. These ports may be arranged to provide a swirling action and thereby induce rotation of the flowing material about the central axis of the conduit at each end.

Desirably, the dielectric structure also defines a second conduit having inlet and outlet ends, the inlet end of the second conduit communicating with the outlet end of the first conduit. The apparatus desirably includes a means defining a third electrode surface adjacent the inlet end of the second conduit and further electrode surface adjacent the outlet end of the second conduit. The third electrode surface may be connected at the same electrical potential with the second electrode. Indeed, the third electrode surface may be defined by a central electrode body which also defines the second electrode surface. The third and fourth electrode surface, and the second conduit, may be configured similarly to the first and second electrode surfaces and the first conduit. Thus, the third and fourth electrodes may have electrode surfaces with areas larger than the minimum cross-sectional area and most desirably larger than the mean cross-sectional area of the second conduit. Typically, in use the second and third electrode surfaces are disposed at the juncture between the first and second conduits and are connected to a source of alternating electrical potential. The first and fourth electrode surfaces, disposed at the inlet end of the first conduit and at the outlet end of the second conduit, are connected to ground.

The apparatus may include means for adjusting the geometry of one or more of the conduits without disassembling the apparatus so as to control the electrical resistance of the material in the conduit. Preferably, this means for adjusting includes means for varying the diameter of at least one such conduit at least one such point along its length. Most desirably, a tube defining such conduit is formed from a flexible material and the means for varying includes means for pressurizing the exterior of the flexible tube so as to deform the wall of the flexible tube inwardly. As further discussed below, this control means can be actuated using opened loop or, more preferably, closed loop control systems so as to maintain desired process conditions.

Electroheating apparatus according to a further aspect of the invention includes first and second electrodes having exposed first and second electrode surfaces and further includes a dielectric structure defining a continuous open course extending between these surfaces. The dielectric structure defines a region of the course remote from the electrode surfaces having a cross-sectional area substantially smaller than the area of each such electrode surface. The apparatus further includes means for admitting a conductive fluid material to the course and discharging the fluid from the course so that at least some of this material passes through the aforesaid region of the course and so that at least some of the conductive fluid material contacts the electrode surfaces. Thus, the conductive fluid material will form an electrically conductive path between the electrode having electrical resistance in the aforesaid region of the course substantially greater than the electrical resistance of the path adjacent the electrode surfaces. Most desirably, the first and second electrode surfaces are disposed at substantially uniform distances from one another such that the length of the shortest path from a point on the first electrode surface through the aforementioned open course to a point on the second electrode surface is substantially the same for any points on the first and second electrode surfaces. Stated another way, the electrode surfaces, and the dielectric structure defining the course, are so constructed and arranged that the path from any point on the first electrode to any point on the second electrode has substantially the same length, and hence the same electrical resistance, as the path from any other point on the first electrode to any other point on the second electrode. This promotes substantially uniform current distribution over the electrode surfaces in use. One such uniform length, uniform resistance arrangement is provided by spherical surfaces disposed outside of the ends of a relatively small diameter conduit where the center of each spherical surface is adjacent the opening of the conduit.

Yet another aspect of the present invention includes the discovery that carbonaceous electrode surfaces such as graphite provide markedly superior results in electroheating, particularly electroheating of proteinaceous substances including food products such as egg. This aspect of the present invention thus provides apparatus for electroheating including dielectric structure defining a chamber, which may have any configuration but which desirably includes a course or conduit as discussed above, and electrodes having exposed surfaces in the chamber, the exposed surfaces consisting essentially of carbonaceous materials, most. preferably graphite. This aspect of the present invention further provides methods of electroheating in which a fluid to be heated is contacted with electrodes so that the fluid contacts only carbonaceous surfaces of the electrodes and so that electrical current is passed through the fluid by way of the carbonaceous surfaces on the electrodes. The carbonaceous electrodes not only resist corrosion damage but also minimize gas formation and other electrolysis effects in the fluid being processed. This effect is particularly advantageous when combined with the beneficial effects of the other aspects of the invention discussed above, but can be applied in other electroheaters as well.

These and other objects, features and advantages of the present invention will be more readily apparent from the detailed description of the preferred embodiments set forth below, taken in conjunction with the accompanying drawings.

BRIEF DESCRIPTION OF THE DRAWINGS

FIG. 6 is a diagrammatic sectional view depicting apparatus in accordance with a further embodiment of the invention.

FIG. 7 is a diagrammatic view similar to FIG. 3 but depicting apparatus in accordance with a further embodiment of the invention.

FIG. 8 is a diagrammatic view similar to FIG. 3 but depicting apparatus in accordance with yet another embodiment of the invention.

FIG. 9 is a diagrammatic sectional view depicting apparatus in accordance with still another embodiment of the invention.

FIG. 10 is a further diagrammatic sectional view depicting apparatus in accordance with another embodiment of the invention.

FIG. 11 is another diagrammatic section view, similar to FIG. 10 but depicting apparatus in accordance with yet another aspect of the invention.

DETAILED DESCRIPTION OF THE PREFERRED EMBODIMENTS

General System Operation

Figure 1:
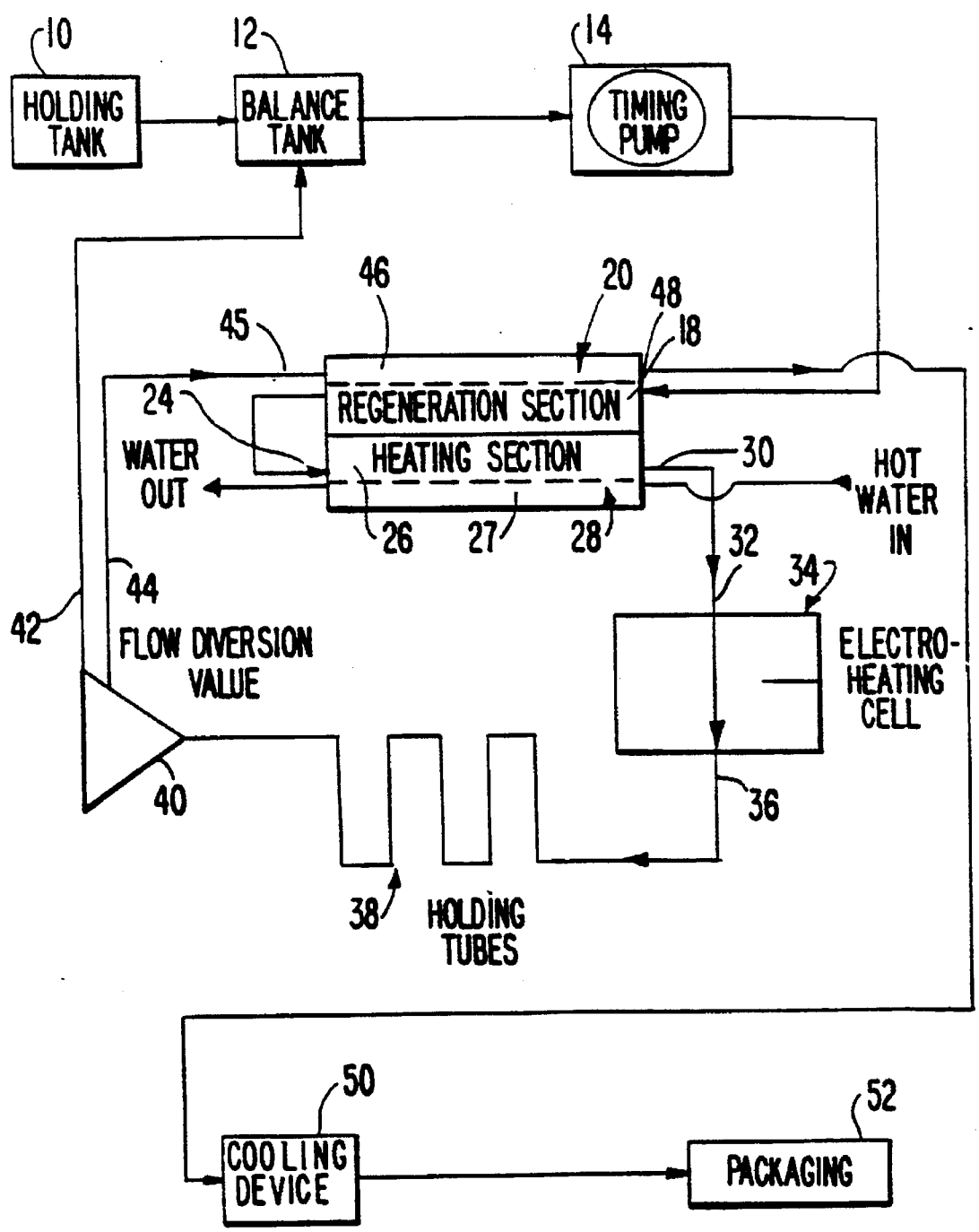
FIG. 1 is a schematic flow diagram of a pasteurization system incorporating electroheating apparatus and methods in accordance with one embodiment of the invention.

A pasteurization system in accordance with one embodiment of the present invention incorporates a holding tank 10 for retaining an electrically conductive fluid material to be processed. A balance tank 12 is connected to the holding tank, and an outlet from the balance tank is connected to the inlet of a timing pump 14. The output of timing pump 14 in turn is connected to a product side 18 of a plate-type heat exchanger 20 referred to as the "regeneration section". The outlet of product side 18 is connected the inlet of a product side 26 of another plate-type heat exchanger 28 referred to as the heating section. The outlet of product side 26 in turn is connected to the inlet 32 of an electroheating cell 34. The outlet 36 of the electroheating cell 34 in turn is connected to a set of holding tubes 38, connected to in series with one another. The last holding tube in the series is connected to the inlet of a flow diversion valve 30. The flow diversion valve is arranged to direct material from the holding tubes through a first outlet 42 if the temperature of the material is below a preselected minimum and to direct the material through a second outlet 44 if the temperature of the material is above the preselected minimum. The first outlet 42 of flow diversion valve 40 is connected to balance tank 12, whereas the second outlet 44 is connected to the inlet of a hot side 46 in regeneration section heat exchanger 18. The outlet of hot side 48 in turn is connected to an inlet of a refrigeration cooling device 50. The outlet of hot second side 48 in turn is connected to an inlet of a refrigeration cooling device 50. Fluid material passing through the hot side 46 of regeneration section heat exchanger 18 will be in thermal exchange relationship with material on the product side 18 of the regeneration section heat exchanger, but will not be in contact therewith. Stated another way, the regeneration section heat exchanger permits exchange of heat between the material on the hot side and the product side, but prevents commingling of these materials. Heating section 28 also has a hot side 27 in thermal exchange relationship with first side 26 but not in communication therewith. An inlet of hot side 27 is connected to a source of hot water (not shown) and an outlet of the hot side 27 is connected to a water outlet, which in turn feeds back into the hot water source for reheating.

Cooling device 50 is arranged to bring the material passing through it to a temperature suitable for packaging. The outlet of the cooling device is connected to the product inlet of packaging equipment 52. Cooling apparatus 50 may incorporate a mixing device for mixing previously cooled material with the material passing from the system. One such mixing device is a so-called "y-shaped" mixer as described, for example, in the U.S. Pat. No. 5,290,583. Such device has two inlet conduits and an outlet conduit, the inlet conduits merging with one another in a mixing chamber so that hot material can be intimately admixed with cold, already pasteurized material and chilled rapidly. Such mixing devices can also be used immediately downstream from the outlets 44 of the flow diversion valve so as to cool the material almost instantaneously from above the required minimum temperature as it exits from the holding tubes 38.

Apart from electroheating cell 34, the aforementioned elements of the apparatus may be of generally conventional construction. Where the material to be processed is food product, a medical product, body fluid or other product requiring sanitary precautions, the elements of the apparatus discussed above are constructed in accordance with conventional sanitary engineering standards and practices.

In general, the pasteurization system operates as follows: material to be pasteurized passes from the holding tank 10 through the balance tank 12 and timing pump into the product side 18 of the regeneration section, where it is initially preheated by thermal exchange from outgoing material. The incoming material from the product side of the regeneration section is then further preheated by thermal exchange from hot water in the heating section 28, whereupon the material passes into the electroheating cell 34. As further discussed below, the material is rapidly heated in the electroheating cell to above the desired minimum pasteurization temperature. The heated material remains as close to this peak temperature as it passes through insulated holding tubes 38. The time for the material to pass from the outlet 36 of the electroheating cell to flow diversion valve 40 is fixed by the geometry of the system and the flow rate established by timing pump 14. This time is selected so that the time for the material to pass from cell 36 to valve 40 is at least as long as the required minimum pasteurization time. Thus, if the material is at a temperature above the minimum pasteurization temperature when it arrives at diversion valve 40, it is known that the material has been held at above the minimum pasteurization temperature for at least the required pasteurization time. Provided that the material is at the required temperature, it passes through outlet 44 to the second side 46 of the regeneration section heat exchanger, where it gives up some heat to incoming material and drops rapidly below the minimum pasteurization temperature and then passes to cooling section 50 where it is brought to the desired temperature for packaging. However, if the material reaching flow diversion valve 40 is not at the required minimum temperature, it passes back through outlet 42 to the balance tank 12 where it is passed again through timing pump 14 and through the process once again.

Electroheating Cell Construction

Figure 2:
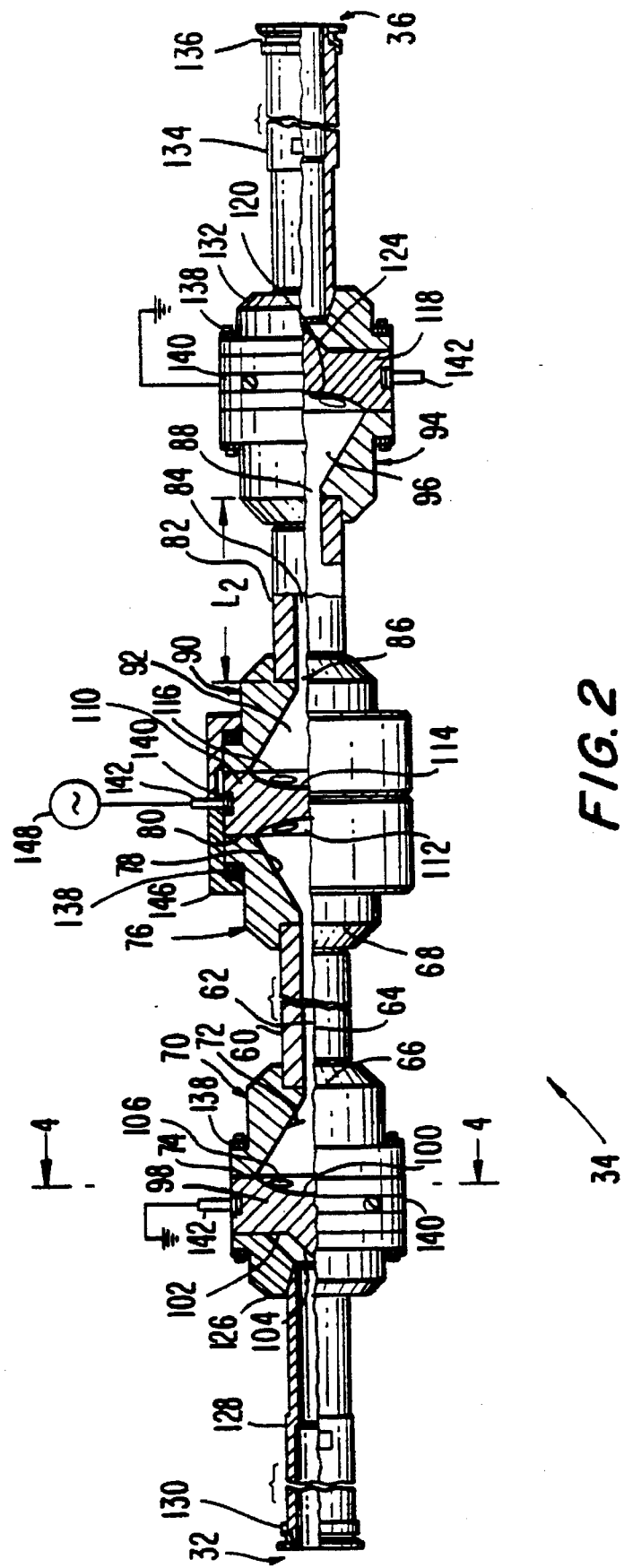
FIG. 2 is a diagrammatic sectional view of an electroheating unit utilized in the system of FIG. 1.
Figure 4:
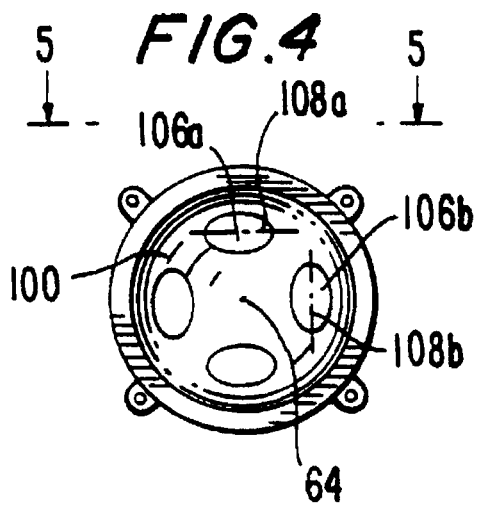
FIG. 4 is a sectional view taken along line 4—4 in FIG. 2.
Figure 5:
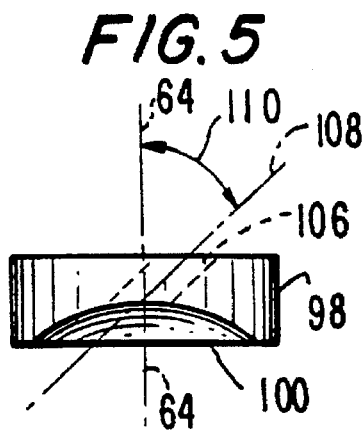
FIG. 5 is a top plan view taken along line 5—5 in FIG. 4.
Figure 3:
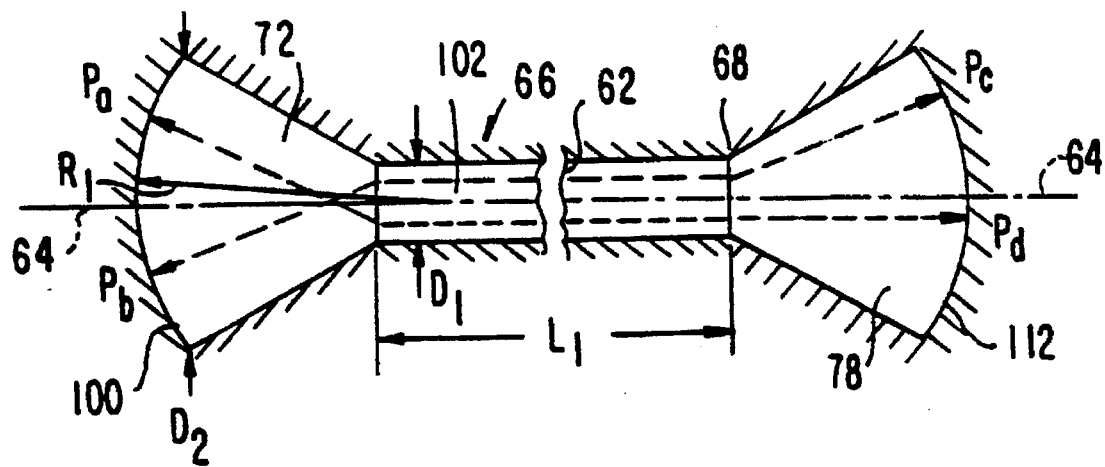
FIG. 3 is a diagrammatic view depicting portions of the apparatus shown in FIG. 2.

Electroheating cell 34 is shown in greater detail in FIGS. 2–4. The direction from the inlet 32 of the cell to the outlet 36 is referred to herein as the "downstream" direction of the cell, whereas the opposite direction is referred to as the "upstream" direction. The cell includes a dielectric structure including a first elongated dielectric tube 60 defining a first elongated cylindrical conduit 62. Conduit 62 has a central axis 64, an inlet end 66 and an outlet end 68. Conduit 62 is circular in cross-section and has a constant diameter $D_1$ (FIG. 3). The length $c_1$ of tube 60 and conduit 62 is shortened in FIG. 2 for illustrative purposes; in actual practice, the length of the conduit may be many times its diameter The dielectric structure further includes a first or upstream transition section 70 having a wall defining a generally conical transition passageway 72 coaxial with conduit 62 at the first end 66 of the conduit. Transition passageway 72 has a progressively increasing diameter in the upstream direction, away from inlet end 66 and tapers inwardly in the downstream direction to a diameter $D_1$, equal to the diameter of conduit 62 immediately adjacent the inlet end of the conduit. Transition section 70 has a flat contact face 74 at its end remote from conduit 62, face 74 being substantially perpendicular to the axis 64 of the conduit and transition passageway. The conical transition passageway 72 forms a circular opening of diameter $D_2$ at face 74.

The dielectric structure further includes a second or downstream transition section 76 associated with the outlet end 68 of conduit 62, the second transition section defining a generally conical second transition passageway 78 merging with the outlet end 68 of the conduit and having progressively increasing cross-sectional area in the downstream direction away from the outlet end 68. Second transition passageway 78 terminates in a circular opening at a flat face 80 on the end of transition section 76 remote from the conduit. The configuration of the second transition section and second transition passageway are essentially identical to that of the first transition section and transition passageway discussed above.

The dielectric structure further includes a second elongated dielectric tube 82 defining a second conduit 84 having an inlet end 86 and an outlet end 88; a third transition section 90 defining a generally conical transition passageway 92 at the inlet end 86 of the second conduit 84 and a fourth transition section 94 defining a conical transition passageway 96 at the outlet end 88 of second conduit 84. Second tube 82, third transition section 90 and fourth transition section 94 are substantially identical to the first tube 60, first transition section 70 and second transition section 76 discussed above, except that the length $L_2$ of the second conduit is slightly greater than the length $L_1$ of first conduit 62, for reasons further discussed below.

The components of the dielectric structure can be fabricated from essentially any dielectric material which has adequate physical and dielectric strength and which is suitable for contact with the material to be treated. In the case of foods, beverages and pharmaceuticals, the materials normally must meet applicable governmental regulations. For typical foods and pharmaceuticals, materials such as acetal polymers such as those sold under the registered trademark DELRIN by the DuPont Company and those sold under the registered trademark CELCON by the Celenese Corporation can be used, as well as glass, certain hard rubber compositions and thermosetting polymers such as phenolics. Polyetherimide resins of the type sold under the trademark ULTEM by the General Electric Co. of Schnectady, N.Y. are especially preferred.

The electroheating unit further includes a first electrode body 98 defining a first electrode surface 100. Surface 100 is a portion of a spherical surface having its center 102 on axis 64, substantially at the apex of the conical transition passageway 72. Stated another way, the generator of the conical surface of the transition passageway passes 72 through or adjacent the center 102 of spherical electrode surface 100. First electrode body 98 has a flat surface mating with the flat surface 74 of the first transition section 70. Spherical surface 100 intersects the flat surface of the electrode body along a circular boundary having a diameter, measured about the central axis 64 substantially equal to the diameter $D_2$ of the open end of the transition passageway or just slightly less than $D_2$. Thus, the wall of the transition section 70 merges with the electrode body around the periphery of spherical electrode surface 100.

First electrode body 98 has an input surface 102 substantially perpendicular to central axis 64 and facing upstream in the opposite direction from spherical first electrode surface 100. A conical flow spreader 104 projects from surface 102 on the central axis 64. First electrode body 98 has four ports 106 extending through it, from surface 102 to surface 100. Each port 106 has a input axis 108 lying in a plane remote from the central axis 64 of the spherical surface 100. Thus, axis 108a of port 106 disposed at the top of the drawing in FIG. 4 lies in a generally horizontal plane above central axis 64, whereas axis 108b of port 106b disposed at the right-hand side of the drawing in FIG. 4 lies in a vertical plane to the right of axis 64 and so on. Each port axis 108 is disposed at an oblique angle 110 to the projection of central axis 64 into the plane of the port axis 108. Stated another way, the axes 108 of all of the ports 106 slope in the same direction with respect to central axis 64 so that the ports are disposed in a generally helical pattern. A particle moving particle moving through any port 106 in the direction from input surface 102 to electrode surface 100 will be moving counter-clockwise to axis 64, as seen from a point on axis 64 downstream of the electrode surface.

The apparatus further includes a central electrode body 110 defining a spherical second electrode surface 112 and spherical third electrode surface 114 arranged back to back. Second electrode surface 112 faces upstream towards the second transition passageway 78 whereas the third electrode surface 114 faces downstream towards third transition passageway 92. Each of these spherical surface 112 and 114 is centered on central axis 64. Each such spherical surface has essentially the same configuration and relationship with the associated transition passageway as discussed above with reference to the first electrode surface 100. Thus, in the same manner as discussed above, the wall of second transition section 76 joins the central electrode body 110 around the periphery of second electrode surface 112, whereas the wall of third transition section 90 joins the central electrode body 110 around the periphery of third electrode surface 114. The central electrode body 110 has four ports 116 of which only some are visible in FIG. 2. Each such port extends through the electrode body from second electrode surface 112 to third electrode surface 114. Ports 116 are disposed in a generally helical arrangement similar to the ports 106 of the first of upstream electrode body 98. That is, the axis of each port 116 is sloped so that a particle moving along the axis of each port 106, from surface 112 to surface 114 will move counter-clockwise around central axis 64 as seen from a point on the central axis downstream from the central electrode body.

The apparatus further includes a third or downstream end electrode body 118 defining a fourth electrode surface 120. Body 118, electrode surface 120 and their relationship with the associated fourth transition section 94 are identical to the corresponding features of the upstream, first electrode body 98 and the associated first transition section 70. However, the fourth electrode surface 120 faces upstream whereas the spreader 124 of the downstream electrode body faces downstream.

The apparatus further includes an inlet cover 126 attached to the upstream or inlet face 102 of the first, upstream electrode body 98, the inlet cover 126 defining a conical inlet passage extending to the openings of the ports 106 in body 98. An inlet pipe 128 is connected to inlet cover 126. The inlet pipe has a conventional fitting 130 at its end remote from the inlet guide for connection to the remainder of the system. An outlet cover 132, outlet pipe 134 and outlet pipe connection 136, substantially identical to the corresponding inlet features are connected at the downstream end of the downstream electrode body 118.

Each of electrode bodies 98, 110 and 118 can be formed from substantially any electrically conductive material which is acceptable for contact with the material to be processed and which resists corrosion and electrolytic effects. Materials such as stainless steel, titanium, nickel and other metals and alloys can be employed. However, carbonaceous materials, i.e., materials consisting essentially of carbon, are particularly preferred. Such materials include graphite, pitch, diamond and diamond-like forms of carbon. Graphite is particularly preferred. One form of graphite which can be used is sintered graphite such as that sold under the designation XT graphite and XT-CF graphite by Poco Graphite Incorporated of Decatur, Tex. The XT-CF graphite is pretreated by an alcohol impregnation process so as to minimize water absorption during use, and is preferred. Another preferred material includes graphite with a surface layer of pyrolytic carbon to reduce porosity. One such material is sold under the designation "PYE COATED" carbon by Poco Graphite Incorporated. The entire electrode can be formed from sintered graphite. Alternatively, a carbonaceous material can be applied over a metallic body, so that the surface in contact with the product being treated is formed from the carbonaceous material. The carbonaceous materials, and particularly graphite, resist electrolysis and corrosion in service. Moreover, graphite, as well as other carbonaceous materials, tends to minimize electrolysis of the product being treated and, particularly, tends to suppress gas formation. The advantageous properties of the carbonaceous electrodes can be applied in electroheating apparatus of any configuration. Each electrode body is provided with a band 140 of a highly conductive material such as copper and encircling the exterior surface of the electrode body, remote from the material to be processed. Each band is connected to a tap 142 for connection of the electrode to an external potential.

The electrode bodies are secured to the adjacent components by bolts 138 passing through the electrodes outside the periphery of the electrode surfaces. The central electrode body 110 and the associated bolts are covered by a protective shroud 146 formed from a dielectric material. O-rings or similar seals may be provided between the surfaces of the electrodes and the mating surfaces of the other components. The tubes 60 and 62 defining the first and second conduits may be secured to the transition sections by threaded fastening, slip fit fastening or other conventional fastening arrangements. Of course, where used in contact with food, pharmaceuticals or other materials requiring sanitary precautions, the various components should be designed in accordance with known principles of food equipment engineering, and in accordance with applicable codes and standards, so as to facilitate cleaning and prevent build-up of contaminated material within the apparatus.

The upstream or inlet end electrode body 98 and the downstream or outlet end electrode body 118 are both connected to ground potential, whereas the central electrode body 110 is connected to a mains frequency alternating potential source 148, arranged to apply a potential with respect to ground alternating at a preselected frequency, desirably less than about 100 Hz and more desirably about 50–60 Hz. Source 148 may include a direct connection between the electrode body 110 and the utility line or else may include a transformer (not shown) interposed between the electrode 110 and the utility power line.

Electroheater Operation

In operation, material to be treated, preheated in the regeneration section 20 and heating section 28 of the heat exchange (FIG. 1) passes into the inlet 32 of the electroheating cell, and thus passes through the inlet pipe 128 and inlet cover 126. The flowing material diverges outwardly around the spreader 104 of upstream electrode body 98 and passes through the ports 106 in the electrode body. As the material passes through the port, it enters the first transition passageway 72 with a swirling motion, in the counterclockwise direction around the central axis 64, and passes through the first conduit 62 and through the second, conical transition passageway 78 to central electrode body 110. The material passes through the ports 116 in the central electrode body, and again is guided into a swirling motion about the central axis 64. It passes downstream through the third transition section and the second conduit 84 to the fourth transition passageway 96 and then flows through the ports of the downstream electrode body 118 and out through the outlet cover 132 and outlet pipe 134 to the outlet 36 of the electrode heating unit. The swirling motion of the material passing through the unit helps to assure that the material does not stagnate at any point within the unit.

As the electrically conductive, flowing material passes through the unit, it contacts the electrode surfaces. Thus, the material momentarily positioned between the upstream electrode body 98 and the central electrode body 110 is in electrical contact with the first electrode surface 100 and the second electrode surface 112. Source 148 imposes a potential difference between these two electrode surfaces, causing current to flow through the material and heat the material. This current is substantially uniformly distributed over electrode surfaces 100 and 112. As best illustrated in FIG. 3, each electrode surface lies at a substantially uniform distance from the associated opening of conduit 62. Thus, any point on first electrode surface 100 lies at a distance approximately equal to the radius $R_1$ of surface 100 from the first or upstream end of conduit 66 whereas any point on second electrode surface 112 lie at substantially the same distance from the end or downstream end 68 of conduit 62.

As the openings of the conduit are circles of finite diameter $D_1$, the distance from a given point on an electrode surface to one point within the opening may differ slightly from the distance from the same point on the electrode surface to another point in the same opening. However, the diameter $D_1$ of the openings is substantially smaller than the radius $R_1$ of each electrode surface. Typically, the ratio to electrode surface radius $R_1$ is at least about 2½:1, and most preferably more than about 6:1. With this electrode surface configuration, the shortest path from any point on electrode 100 to another point on second electrode surface 112 is substantially the same for any pair of points on the two surfaces. That is, the shortest path from point $P_a$ through conduit 62 to point $P_c$ on second electrode surface 112 would be substantially the same as the length of the shortest path from point $P_b$ on the first electrode surface to point $P_c$, and these lengths in turn would be the same as the shortest path length from point $P_a$ or point $P_d$ on first surface 100 to point $P_d$ on second surface 112. Preferably, the shortest path lengths for any points on the surfaces differ by less than about 5 percent.

Because the path length from any point on the first electrode surface to any point on the second electrode surface is substantially the same, the electrical resistance from any point on the first electrode surface 100 to any point on the second electrode surface 112 is substantially the same as the electrical resistance for any other points on the two surfaces. Therefore, electrical current passing between first electrode surface 100 and second electrode surface 112 is substantially uniformly distributed over both of these electrode surfaces. The maximum current density at any point on the electrode surface desirably is no more than about 105% of the average current density for the entire electrode surface. Thus, the maximum and average current density at the electrode surface is substantially equal to the total current divided by the area of each electrode surface.

Because the cross-sectional area of conduit 62 is substantially smaller than the cross-sectional area of the electrode surfaces, the current density and the electrical resistance per unit length along axis 64 are substantially higher in the conduit than in the transition passageways adjacent the electrode surfaces. Preferably, the ratio between the area of each electrode surface and the mean cross-sectional area of conduit 62 is at least about 5:1, preferably at least about 10:1 and most preferably at least about 35:1 or more. The ratio of the maximum current density in the conduit to the current density at the electrode surface will have similar values, as will the resistance per unit length along the upstream-to-downstream axis 64. At any point along the upstream-to-downstream axis, the rate of power dissipation and the rate of heat evolution is $I^2R$, where I is the current and R is the resistance at such point. I is the same at all points, whereas R is very low adjacent the electrodes and very high within conduit 62. Thus, essentially all of the electrical energy dissipated between the first electrode surface and the second electrode surface is dissipated in conduit 62. The flowable material passing through the system is substantially heated by internal resistance heating while passing through the conduit, but is not substantially heated in the vicinity of the electrode surfaces.

Exactly the same relationships apply with respect to the material momentarily disposed between third electrode surface 114 and fourth electrode surface 120. Once again, essentially all of the heating will occur inside conduit 84, and little or no heating will occur within the transition passageways 92 and 96.

Because the upstream or inlet end electrode body 98 and downstream or outlet electrode body 118 are both maintained at ground potential, there is essentially no leakage of electrical current from the electroheating unit to the other portions of the system.

Process Parameters

Essentially any amount of heat can be provided to the material passing through the electroheating cell. One method of selecting process parameters starts with the amount of heat to be applied in the electroheater. That amount in turn is determined by the desired temperature entering the preheater 32, the temperature desired at the electroheater output 36, the mass flow rate of material per unit time and the specific heat of the material. The product of the difference between inlet and outlet temperatures, the flow rate and the specific heat gives the needed energy input per unit time in the entire electroheater. For a system with two separate heating regions and four electrode surfaces, the total energy input is divided as desired to give the desired energy input per unit time per region. The energy input per unit time of course converts directly to power. Typically, the energy input is calculated in kilocalories/Hr and this number divided by 860 yields the electrical power in kilowatts required.

Essentially any voltage may be used. Voltages of about 100 volts to about 15 Kv are readily available in industrial power systems. Voltages above about 220 volts, are preferred. The applied voltage may have any frequency from $\emptyset$ (DC) to radio frequencies, typically up to about 500 KHz. Line frequency below 100 Hz is preferred and about 50–60 Kz is especially preferred. Assuming that the available voltage from source 148 is fixed, division of the calculated power by the voltage yields the required current flow for each pair of electrodes. The required resistance between electrodes is calculated by dividing the assumed voltage by the calculated current flow. Once the calculated resistance has been found, the dimensions of the cell are effectively fixed. Using the assumption that substantially all of the electrical resistance between the electrodes is in the conduit, the resistance is substantially equal to $$R = \frac{L_c}{A_c C}$$

where R is the electrical resistance in ohms;

$L_c$ is the length of the conduit;

$A_c$ is the cross sectional area of the conduit; and

C is the specific electrical conductivity of the material being heated, expressed as $MHO/cm/cm^2$.

The cross-sectional area typically is selected to accommodate the flow of the fluid with a reasonable pressure drop. For a given material and for a given conduit cross-sectional area, $L_c$ is directly derivable from the desired resistance value R:

$$L_c = R A_c C.$$

The value of conductivity C will vary with the material and will also vary with the temperature of the material itself. Thus, as the material is heated the value of C typically increases. In typical processes, a reasonably accurate estimate of C for each section can be obtained by taking the arithmetic mean between the value of C at the inlet to the section and the value of C at the outlet. Where the material is heated through a very large temperature range, or where the variation of C with temperature for the material is particularly large, a more accurate value of C can be obtained by plotting the logarithm of C against temperature and determining the value for the logarithm of C at a mean between the inlet temperature to be sectioned and the outlet temperature from the section. In a four-surface, two-section unit as illustrated in FIG. 2, the material passing through the second section will have a substantially higher mean temperature than the material in the first section and thus a higher value of C. To provide equal currents and equal power division between the two sections, the value of $L_C$ for the second or downstream section will be greater than the value of $L_C$ for the first or upstream section; the second conduit 84 will be longer than the first conduit 62. Alternatively, the second conduit can be formed with a somewhat smaller cross-sectional area $A_c$. However, equal power division between the two sections is not essential. In many cases, the downstream section has equal or small conduit length than the upstream section, so that the downstream section carries more power and provides a higher heating rate than the upstream section.

For many materials there is a critical, maximum current density which can be tolerated at the electrode surface. This critical current density can be determined by testing the material at progressively increasing current densities until arcing occurs at the electrode surface. For liquid egg, as defined hereinbelow, the critical current density is approximately 0.25 amps/cm$^2$. For whole milk, the critical current density is about 0.40 amps/cm$^2$ and for 0.5 percent saline solution, the critical current density is about 1.0 amps/cm$^2$. Thus, the required current is divided by the area of the electrode surfaces. If the result is below the critical current density for the material, the result is satisfactory. If not, the current must be reduced either by increasing the number of regions, and hence the number of electrodes, by raising the resistance of each stage or by increasing the surface area of the electrodes.

The heating time in the electroheater is directly related to the volume of the electroheater (principally the volume of the conduits 62 and 84) and inversely related to the flow rate of the material. The internal volume of the heater can be controlled by controlling the diameter of the conduits 62 and 84. As the diameter and hence the cross-sectional area of the conduits are reduced, the conduit length can remain the same if the voltage is increased, or else can be reduced to maintain a constant resistance. Either approach leads to a shorter residence time. The lower limit on the conduit internal diameter is set by considerations of increasing flow resistance at smaller diameters, which lead to extremely high pressures within the system and high pumping loads and by considerations of mechanical shear damage to the product. However, in practical systems, the residence time of the material within the electroheater may be only a small fraction of a second, and the heating rate may be hundreds or even thousands of degrees per second.

Numerous variations and combinations of the features discussed above can be utilized without departing from the present invention.

Additional Structures

As illustrated in FIG. 6, one such variant includes a first or upstream body 298 defining a first electrode surface 200; a central electrode body 210 defining a second electrode surface 212 and third electrode surface 214 and a downstream or outlet electrode body 218 defining a fourth electrode surface 220. The electrode bodies are substantially similar to the electrodes discussed above with reference to FIGS. 2-5. Also, the apparatus of FIG. 6 includes a dielectric structure having a first, rigid tube 260 defining a first conduit 262 and also having transition sections 259 and 261 connecting the ends of the conduit 262 with a first and second electrode surface 212. These elements are also similar to the first tube and transition sections discussed above. The dielectric structure in FIG. 6. however includes a flexible, elastomeric tube 282 defining the second conduit 284, disposed between the third electrode surface 214 and the fourth electrode surface 220. Conduit 284 is connected by rigid transition sections 290 and 294 to the electrode bodies 210 and 218, the transition sections being similar to those discussed above. A hollow dielectric shell 285 surrounds the exterior of tube 282 and defines a sealed space 283 between the exterior of the tube and the interior of the shell.

Space 283 is connected to a gas source 285 and vent 287 by an electropneumatic control system 289. A current sensor 271 is connected between the downstream or outlet end electrode body 218 and ground, whereas a similar sensor 273 is connected between the inlet, upstream end electrode body 298 and ground. As in the embodiment discussed above, the central electrode body 210 is connected to an alternating current potential source. Sensors 271 and 273 are connected to the control system 289. In operation, control system 289 compares the readings from the two sensors. The reading of sensor 273 gives the current flowing in the first heating region, through conduit 262 from the center electrode body to the upstream electrode body 298. Sensor 271 reads the current flowing in the second or downstream heating region, within conduit 284. If the current in the second region, detected by sensor 271, exceeds the current in the first region, the control means admits gas 285 into space 283 so as to raise the pressure therein and deform tube 282 inwardly, thus bringing the tube to the position illustrated in broken lines in FIGS. 6–7. This reduces the cross-sectional area of conduit 284, thereby increasing the electrical resistance in the second or downstream section and reducing the current. If the current in the second section falls below that in the first section, the control system 289 actuates vent 287 to release some of the gas from space 283, thereby reducing the pressure, allowing the wall of tube 282 to bulge outwardly back towards the position illustrated in solid lines or even further outwardly, thereby increasing the mean cross-sectional area of the conduit 284, decreasing the resistance and increasing the current in the second section. In this manner, the system provides control of the resistance, and provides control of the resistance in the second section without disassembly of the apparatus and without interruption of product flow.

In a variant of this approach, the variable diameter conduit could be provided in both sections, and the control means could be arranged to adjust the diameters of both conduits 262 and 282. In such an arrangement, the variable diameter conduits can be employed to adjust the resistance of both sections as required to compensate for changes in the resistivity of the product caused by changes in composition and temperature of the incoming product; to compensate for changes in the amount of heating required, and to compensate for changes in the applied voltage, as well as to balance the current flows between the two sections. All of these changes can be accomplished without interrupting the productivity of the system.

In the arrangement of FIG. 6, the cross-sectional area of the conduit is varied by applying fluid to the exterior of a flexible tube. However, the cross-sectional area can be varied by mechanically pinching a flexible tube between a pair of opposed members. It can also be varied by mechanically pulling the ends of a flexible tube defining the conduit away from one another so as to elongate the tube. This causes the tube to stretch and narrow, thereby reducing the cross-sectional area of the conduit and also causes the length of the conduit to increase, thus additionally raising the resistance. The tube defining conduit may be deformable only in the lengthwise direction, as where the tube is formed from several sections telescopically received in one another. Therefore, the length of the conduit may be increased or decreased without appreciably altering the diameter, and without disassembly. This effect provides similar control of capabilities to those discussed above. In yet another variable geometry arrangement, one or more dielectric elements may be mounted within the conduit so as to occlude a portion of the conduit. These elements may be mounted for movement relative to the conduit or relative to one another so as to vary the degree of such occlusion and thereby vary the mean, cross-sectional area of the conduit. For Example, the tube may be provided with a conical valve element movable along the axis of the conduit and a conical valve seat fixed in the conduit so that the valve element can be moved towards and away from the seat.

In the arrangements discussed above, the conduits are straight circular cylinders of uniform diameter and coaxial with one another. The electrode surfaces are spherical regions concentric with the single axis of the cylinders. However, other arrangements may be employed. As illustrated in FIG. 7, the conduit 362 defined by the dielectric structure 360 may be a passageway of generally circular cross-section but of arbitrary configuration such that the central axis of the conduit turns in varying directions along the length of the conduit. In this case, the conduit nonetheless defines a central axis 364 at its inlet end and another, different central axis 365 at its outlet end. A first electrode surface 300 in the form of a surface of revolution may be concentric with the axis 364 at the inlet end of the conduit whereas a second electrode surface 312 may be concentric with the axis 365 of the conduit at the outlet end. The conduit may have other shapes such as a U-shape or helical shape to provide a compact assembly.

It is not essential that the conduit have a circular cross-section. As illustrated in FIG. 8, the conduit 462 defined by the dielectric structure 460 may have a generally rectangular cross-section. Thus, one cross-sectional plane of the conduit is shown in broken lines after 463 in FIG. 8. The conduit has an inlet end 466 and an outlet end 468. The opening at inlet end 466 has a long axis $A_{l1}$ and a short axis $A_{s1}$ perpendicular thereto. The first electrode surface 400 adjacent the inlet end of the conduit is substantially in the form of a cylinder having its axis coincident with the long axis $A_{l1}$ of the adjacent conduit opening. Likewise, the opening of the conduit at the outlet end 468 is generally in the form of a highly elongated, narrow rectangle having a short axis $A_{s2}$ and a long axis $A_{l2}$. The second electrode surface 420 is substantially in the form of a portion of a circular cylindrical surface having an axis coincident with the long axis $A_{L2}$ at the opening 468. Each of the transition passageways is generally in the form of a V-shaped channel with the narrow end of the V at the end of the conduit and with the wide end of the V intersecting the electrode surface.

Here again, the cross-sectional area of the conduit, taken in a plane such as plane 463 perpendicular to the length of the conduit is substantially less than the area of each electrode surface 400 and 420. In use, an electrically conductive material may be passed through the conduit lengthwise, in the flow direction denoted by arrows $F_1$. An electrical potential may be applied between the electrodes 400 and 420, and will provide a current density within the conduit substantially higher than the current density at the electrodes. Here again, the shortest path between any point on electrode 400 and any point on electrode surface 420 via the course or conduit 462 will have substantially the same length as the shortest path between any point on electrode surface 400 and any other point on electrode surface 420. That is, the shortest path distance between any two points on the electrode surfaces is substantially the same regardless of the particular points selected. Accordingly, the current will be substantially uniformly distributed over the electrode surfaces. The ends of the transition passageways and the edge of the conduit visible at the front of the drawing in FIG. 8 are blocked by further dielectric walls (not shown) and the electrodes are provided with appropriate ports (not shown).

In a system according to yet another embodiment, the electroheater includes a first, generally plate-like conductive electrode 500 and a second plate-like conductive electrode 520. The dielectric structure includes a dielectric tube 560 extending between the electrodes and a dielectric packing including a large number of small spheres, chips, rings or other pieces of dielectric material disposed within the dielectric tube intermediate between the electrodes. The tube and packing cooperatively define a large number of parallel continuous paths 510 extending between electrode 500 and electrode 520. These paths extend through interstices between the particles of the packing and join with one another at various points within the packing. However, the various paths can be said to cooperatively define a unified continuous course extending between the electrodes. The continuous course has a cross-sectional area, taken in any arbitrary cutting plane 563 perpendicular to the length of the course (perpendicular to the electrode to electrode direction) equal to the aggregate cross-sectional area of the individual continuous paths. Within the packing this aggregate cross-sectional area is substantially less than cross-sectional area of tube 560 and substantially less than the surface area of the electrode surfaces defined by electrodes 500 and 520.

Apparatus according to this embodiment can be used in substantially the same manner as that described above. Here again, because the cross-sectional area of the course remote from the electrodes is substantially smaller than the surface area of the electrode themselves, the current density within the course (in the interstices between the packing particles) will be substantially greater than the current density at the electrodes. The size of the packing particles is exaggerated in FIG. 9 for clarity of illustration. In actual practice, the packing particles may be very small by comparison to the size of the electrodes and in comparison to the diameter of tube 562. Accordingly, the openings of the various continuous paths at the surfaces of the packing can be substantially uniformly distributed over the ends of the packing, so as to provide substantially uniform path lengths between any points on the surfaces of the electrodes.

The methods and apparatus according to the present invention can also be used to heat slurries and particulates. The term "slurry" as used herein refers to any mixture of solid particles in a liquid phase. Thus, many common industrial and food products are slurries, such as stews, soups and the like. Food products containing plant or animal tissues desirably are maintained under pressure while passing through the electroheating apparatus. The pressure minimizes tissue damage and consequent loss of texture during the heating operation. Also, where a particulate solid must be heated, the particles can be mixed with a carrier liquid to form a temporary slurry for electroheating. The liquid phase should have at least some electrical conductivity so that current can be transferred from the electrodes, through the liquid phase to the particles as the slurry passes through the electroheater. However, it is desirable to concentrate the flow of current through the particles, rather than through the liquid phase. The ratio of particle volume to fluid volume should be as high as possible consistent with the ability to pump the slurry. With large, non-compressible particles, a typical slurry may contain about 70 percent particles by volume.

Desirably, the liquid phase has a lower conductivity than the particles. This can be achieved through control of the fluid composition itself as, for example, by using wholly or partially deionized or distilled water in the liquid phase. Alternatively, the relative conductivities of the particles and fluid can be controlled by controlling the temperature of the two phases as they enter the electroheater. Where conductivity of the particles increases with increasing temperature, the particles can be preheated either by a preliminary electroheating operation or by conventional, conductive, microwave or other heating. If only the outer layers of a particle are preheated, the current will concentrate in the outer layers, and may leave the center of each particle inadequately heated. Therefore, the particle preheating may be conducted by first applying heat to the particles and then allowing the particles to dwell and come to thermal equilibrium before electroheating. Desirably, the preheating operation and dwell operations are conducted so that the preheated particles, after the dwell time, have center temperatures slightly higher than the exterior temperatures of the particle, thereby assuring that the current will pass through the center of the particle.

Alternatively or additionally, the liquid phase can be cooled prior to formation of the slurry. The residence time of the particles and the liquid in the electroheater can be very short, on the order of a second or even less. In this time, there will not be appreciable heat transfer between the liquid and the solid particles. By cooling the liquid, its specific conductivity will be reduced, thus tending to concentrate more of the current in the electroheater within the particles.

The nature of the electroheating process reinforces the effects of any attempts to concentrate the current within the particles. That is, if the particles and liquid are introduced into the electroheater under conditions which tend to promote current flow through the particles rather than through the liquid, the particles will be heated more than the liquid, reducing the resistance of the particles more than the liquid and concentrating the current flow to an even greater degree in the particles.

Apparatus according to yet another embodiment of the present invention is illustrated schematically in FIG. 10. The apparatus of FIG. 10 includes a first electrode 600, a second electrode 612 and a dielectric structure 660 defining a course between these electrodes. Here again, the course includes a first, tapered transition passageway 672 adjacent the first electrode, a second tapered transition passageway 678 adjacent the second electrode and a relatively narrow conduit 662 between these transition passageways. The course is subdivided by an upstream porous barrier 601 between the first transition passageway 672 and conduit 662 and by a downstream porous barrier 603 between the conduit and the second transition passageway 678, so that the porous barriers effectively subdivide the course into three zones: a first zone consisting of transition passageway 672 disposed adjacent first electrode 600; a second zone consisting of the conduit 662 and a third zone consisting of transition passageway 678 adjacent the second electrode. The dielectric structure has a fluid inlet 605 communicating with central zone or conduit 662 adjacent upstream barrier 601 and outlet 607 communicating with the central zone adjacent the opposite, downstream barrier 603. First zone 672 also has an inlet 673 and an outlet 675, whereas the second zone 678 has an inlet 679 and an outlet 681. The inlet and outlet of zone 672 are connected to an electrolyte supply apparatus 683 whereas the inlet and outlet of zone 678 are connected to a separate electrolyte supply apparatus 685.

As in the embodiments discussed above, first electrode 600 and second electrode 612 are connected to a source of electrical power (not shown). Each electrolyte supply apparatus is arranged to circulate an electrolyte as further discussed below through the associated zone of the apparatus and to maintain the electrolyte in such zone under a preselected pressure.

In operation, the central zone inlet 605 is connected to a source of product to be treated whereas the central zone outlet 607 is connected to a product receiving device as, for example, the heat exchangers and cooling devices discussed above. The product to be treated is passed through the central zone, but does not pass through the first zone 672 or third zone 678 of the path. The electrolytes within these zones conduct the current from the electrodes to the porous barriers 601 and 603. The porous barriers also contain some of the electrolyte and hence the electrolytes in the porous barriers conduct the current through the barriers to the material being treated in the central zone.

The use of electrolytes and porous barriers between the electrodes of an electroheating system and the product being treated is disclosed in my previous, commonly-owned copending U.S. patent application Ser. No. 08/125,933, the disclosure of which is hereby incorporated by reference herein. As set forth in greater detail in said '933 application, porous barriers 601 and 603 may be formed from ceramic materials such as those sold by the Coors Ceramic Company, having a porosity (for water) of at least about $5.0 \times 10^{-2}$ cc/cm$^2$-Hr-PSI, wherein PSI refers to pounds per square inch. The maximum porosity should be about 5.0 and the preferred porosity is about 0.3, all in the same units of porosity. The porous barriers may be about 3 mm thick and desirably less than about 1.5 mm thick. The barriers may be structurally reinforced.

Preferably, the electrolyte in each of zones 672 and 678 is under a pressure slightly higher than the pressure of the product being treated, so that the product does not penetrate into the pores of the barriers. The electrolyte should be compatible with the product being treated, so that incorporation of minor amounts of the electrolyte into the product due to seepage through the electrodes will not impair the product quality. Normally, the rate of seepage of the electrolyte through the porous barrier is many orders of magnitude smaller than the rate of product flow through the central zone or conduit 662, so that the electrolyte is added to the product in amounts corresponding to parts per million or less. For food products, aqueous solutions containing salts selected from the group consisting of potassium chloride, sodium chloride, calcium chloride, potassium sulfate and sodium sulfates are preferred, and potassium chloride solutions are especially preferred. Desirably, the electrolyte contains the salt in a concentration such as to impart maximum conductivity to the electrolyte. Potassium. chloride electrolytes desirably contain about 30 percent by weight of potassium chloride. To even further reduce the seepage rate, the electrolyte may contain a food-compatible gelling agent as, for example, about 0.1% to about 0.5% by weight of an alginate.

Apparatus according to yet another embodiment of the invention is illustrated in FIG. 11. This apparatus again includes a dielectric structure 760 defining a course including a first tapered transition passageway 772 at one end of a relatively narrow conduit 772 and a further tapering transition passageway 778 at the opposite end of the conduit. A fluid inlet 705 at the upstream end of the structure and a fluid outlet 707 at the downstream end allow for passage of the electrically conductive fluid to be heated in the upstream to downstream direction, through the transition passageways and conduits.

A first composite electrode structure 700 is defined by a plurality of subelectrodes 701. Each subelectrode in turn includes a porous housing 702 and an interior conductive element 702 disposed within the housing. A conductive electrolyte is maintained within each housing 702 so as to conduct current from the central electrode 703 to the conductive fluid passing through the structure. Each of these subelectrodes 701 may include a generally rod-like structure with arrangement for internal circulation of electrolyte from an external source as disclosed in certain preferred embodiments of the aforementioned U.S. patent application Ser. No. 08/125,933. The electrolytes, ceramics and electrolyte conditions may be as discussed above and as described in said '933 application. The subelectrodes 701 and particularly the external, porous ceramic shells 702 of the subelectrodes, are disposed in a curved array so that each subelectrode is at substantially the same distance from the adjacent opening of conduit 762 as the other subelectrodes in electrode 700. Thus, the subelectrodes cooperatively constitute an electrode disposed at a substantially uniform distance from the conduit opening. Similarly, a second electrode 712 is defined by additional subelectrodes 713, each having the same construction as the subelectrode 701 discussed above. Here again, all of subelectrodes 713 are disposed at a substantially uniform distance from the adjacent opening of conduit 762 so as to cooperatively define an electrode surface disposed at a substantially uniform distance from the conduit opening.

In operation, a power supply or potential source 748 applies a potential, such as an alternating potential as discussed above, across electrodes 700 and 712. All of the subelectrodes 701 constituting electrode 700 are connected in parallel to the same pole of potential source 748, so that all of the subelectrodes 701 are at the same potential. Likewise, all of the subelectrodes 713 constituting electrode 712 are connected to another pole of potential source 748, so that all of subelectrode 713 constituting electrode 712 are at the same potential. Thus, current flows from the subelectrodes constituting electrode 700 to the subelectrodes constituting electrode 712, but there is no current flow between the subelectrodes of each individual electrode.

The principles of the invention are further illustrated by the following illustrative, non-limiting examples:

EXAMPLE 1

Using apparatus substantially as illustrated in FIGS. 1–5, liquid whole egg is pasteurized. The egg passes from the outlet of the heat exchanger heating section 27 to the inlet 32 of the electroheating cell at a preheat temperature of about 55° C. and at a flow rate of about 3 Kg/sec. All of the electrodes have peripheral diameter $D_2$ (FIG. 3) of about 9.1 cm. Both conduits are substantially rigid, have internal diameter $D_1$ of about 1.9 cm. The lengths $L_1$ and $L_2$ of the first and second conduits are each about 25.4 cm. The mean residence time of each particle of liquid egg within the active portion of the electroheater, from the first electrode 106 to the fourth electrode surface 120 is about 0.28 seconds, whereas the residence time within conduits 62 and 82, where the actual heating occurs, is only about 0.056 seconds total. 60 Hz 6000 volt alternating potential is applied to the central electrode body 110. The total current flow from the central electrode body to the upstream and downstream electrode bodies 102 and is about 10 amperes RMS. The current density at the first and second electrode surfaces of 100 and 112 is about 0.77 amp/cm² whereas the current density within conduit 62 is about 2.63 amp/cm². The liquid egg between the first and second electrode provides impedance of about 1200 ohms. The second section, including conduit 84, third electrode surface 114 and fourth electrode surface 120 operates at substantially the same conditions but with slightly higher current flow and current density. The total power dissipated in the system is about 60 KW. The temperature of the liquid egg passing through the electroheater rises by 4.8° C. during its 0.056 second residence time in the conduits, and hence the egg is electroheated at a rate of about 85° C./sec. The liquid egg leaving the electroheater has a temperature of about 60° C., the minimum required pasteurization temperature. It is held for the required time period in the holding tubes 38 for about 3–4 minutes and packed in conventional package for an extended shelf-life liquid egg package. The product has good flavor, texture and shelf-life characteristics. The electroheater operates properly without fouling.

EXAMPLE 2

A proteinaceous blood substitute is electroheated in apparatus including only an electroheater, without another heater, the electroheater being generally in accordance with FIGS. 2 and 3. The dimensions are as follows:

$D_1$ 0.318 cm $D_2$ 4 cm $L_1$ 10.8 cm $L_2$ 10.8 cm The flow rate is about 0.064Kg/sec and the residence time within the conduits is about 0.027 seconds. The temperature of the blood substitute was increased by 58° C. during passage through the electroheater, i.e., a heating rate of 2150° C./sec. The substitute at the exit of the electroheater is at a temperature of about 98° C. The heated blood substitute is held at that temperature for about 0.04 seconds and then rapidly cooled.

EXAMPLES 3–15

The electroheater of Example 1 is used to heat fluids in a circulating route, so that fluid being processed is passed from the outlet of the electroheater to a storage tank and from the storage tank back to the electroheater. Various fluid flow rate are employed, in most cases, about 4,000 Kg/Hr. Other operating parameters are set forth in the table below. The "Total Current" is the inlet current to the central electrode body. This current is equal to the sum of the current from the central electrode to the upstream electrode and the current from the central electrode to the downstream electrode. The inlet temperature is the temperature of the fluid entering the electroheater, whereas the temperature rise is the difference between the inlet temperature and the temperature of the fluid leaving the electroheater.

In Example 3, an aqueous sodium hydroxide solution is heated. In Examples 4 through 15, whole egg is heated. In some of these examples, salt and water are added to the liquid egg. Examples 5 through 14 illustrate the effects of progressively increasing inlet temperature. At constant potential (examples 7–11), the current increases as the resistance of the egg decreases. The power dissipation and hence the temperature rise, increase accordingly. Example 15 is taken after the circulating egg has been allowed to cool somewhat. Notably, the system supplies up to 90 Kw of electrical heating to the circulating liquid egg.

EXAMPLE 3

| EXAMPLE | FLUID | POTENTIAL (VOLTS) | TOTAL CURRENT (AMPS) | TEMP. RISE OF °C. | INLET TEMP. °C. |
|---|---|---|---|---|---|
| 3 | NaOH + H$_2$O | 3400 | 9.5 | 7.2 | 29.7 |
| 4 | Whole Egg | 8000 | 7.4 | 12.2 | 55.2 |
| 5 | Whole Egg | 4000 | 3.5 | 3.7 | 1.6 |
| 6 | Whole Egg | 6000 | 5.5 | 7.4 | 3.9 |
| 7 | Whole Egg | 7000 | 7.0 | 10.5 | 9.4 |
| 8 | Whole Egg | 7000 | 7.5 | 11.1 | 11.6 |
| 9 | Whole Egg | 7000 | 8.5 | 12.5 | 16.7 |
| 10 | Whole Egg | 7000 | 9.2 | 13.9 | 22.7 |
| 11 | Whole Egg | 7000 | 10.0 | 15.3 | 27.8 |
| 12 | Whole Egg | 6000 | 10.0 | 13.6 | 35.8 |
| 13 | Whole Egg | 5400 | 10.0 | 12.2 | 40.8 |
| 14 | Whole Egg | 5000 | 10.0 | 11.7 | 44.4 |
| 15 | Whole Egg | 10000 | 9.0 | 17.8 | 38.6 |

What is claimed is:

1. A method of heating a conductive fluid comprising the steps of:
   (a) passing the fluid through a continuous course defined by a dielectric structure and having first and second ends; while
   (b) passing an electrical current between a first electrode surface adjacent the first end of the course and a second electrode surface adjacent the second end of the course so that the electrical current density at a region of said course remote from said electrodes is substantially greater than the electrical current density near said electrode surfaces and so that the electrical current density near said electrode surfaces is substantially uniform to substantially prevent arcing.

2. A method as claimed in claim 1 wherein said step of passing said fluid through said course is conducted so that said fluid passes from said first end of said course to said second end of said course, whereby said fluid and said current pass codirectionally through said course.

3. A method as claimed in claim 2 wherein the electrical current density is substantially uniform over each said electrode surface.

4. A method as claimed in claim 3 wherein said electrical current density is less than about 0.25 amps/cm$^2$ over each said electrode surface.

5. A method as claimed in claim 3 wherein the ratio of current density in said region of said course to current density at each said electrode surface is at least about 5:1.

6. A method as claimed in claim 3 wherein the electrical resistance between said electrode surfaces through the conductive fluid is at least about 100 ohms.

7. A method as claimed in claim 3 wherein said electrical current is applied at a potential of at least about 1000 volts.

8. A method as claimed in claim 7 wherein said electrical current has a frequency of less than about 100 Hz.

9. A method as claimed in claim 3 wherein said conductive fluid is a food product.

10. A method as claimed in claim 9 wherein said food product is heated at a rate of at least about 40 degrees C./sec as it passes through said course.

11. A method as claimed in claim 9 wherein said food product consists essentially of egg.

12. A method as claimed in claim 1 wherein said fluid is a slurry including particles in a liquid phase.

13. A method as claimed in claim 12 wherein said liquid phase has a lower conductivity than said particles.

14. A method as claimed in claim 13 further comprising the step of adjusting the particles to a temperature higher than the temperature of the liquid phase before said electrical current passes through the slurry.

15. A method of electroheating a biological fluid comprising the steps of passing the fluid between first and second electrodes, the electrodes comprising graphite, so that the fluid contacts the electrodes only at surfaces of the electrodes consisting essentially of pyrolytic carbon to reduce porosity, thereby resisting corrosion damage of the surfaces and minimizing electrolysis effects in the fluid, and heating said fluid by passing an electrical current between said electrodes through said carbon surfaces and said fluid, said heating being substantially remote from said electrode surfaces.

16. A method as claimed in claim 15 wherein said electrical current is an alternating current.

17. A method as claimed in claim 15 wherein the electrical resistance between said carbon surfaces through the conductive fluid is at least about 100 ohms and said electrical current is applied at a potential of at least about 1000 volts.

18. A method as claimed in claim 15 wherein said fluid is liquid egg.

19. A method of electroheating a slurry including solid particles having conductivity which increases with increasing temperature in an electrically conductive liquid phase, the method comprising the steps of adjusting the temperatures of the liquid phase, the particles or both so as to bring the slurry to a thermal condition in which the particles are warmer than the slurry and then passing an electrical current through the slurry, whereby the electrical current will tend to heat the particles by concentrating the flow of electrical current through the particles, rather than through the liquid phase.

20. A method of electroheating particles having conductivity which increases with increasing temperature, the method comprising the step of adjusting the temperatures of the particles to a condition in which the interior of each particles is warmer than the exterior of such particles and then passing an electrical current through the particles, whereby the electrical current will tend to pass through the interiors of the particles to heat the interiors, rather than the exteriors, of the particles.

21. A method as claimed in claim 20 wherein said step of passing an electrical current through the particles is performed while the particles are in a slurry with an electrically conductive liquid.

22. A method as claimed in claim 21 wherein said step of adjusting the temperatures of the particles is performed while said particles are in said slurry.

23. A method as claimed in claim 20 wherein said step of adjusting the temperatures of the particles includes the steps of heating the particles and then holding the particles for a dwell time after heating.

* * * * *